United States Patent [19]

Steltenkamp et al.

[11] Patent Number: 4,562,064
[45] Date of Patent: Dec. 31, 1985

[54] STABILIZING OF CINNAMIC ALDEHYDE-CONTAINING FLAVORS WITH TERPENES AND SESQUETERPENES

[75] Inventors: Robert J. Steltenkamp, Somerset; Miriam L. Douglass; Gerard E. Natarelli, both of Piscataway, all of N.J.

[73] Assignee: Colgate-Palmolive Company, New York, N.Y.

[21] Appl. No.: 578,457

[22] Filed: Feb. 9, 1984

[51] Int. Cl.⁴ .......................... A61K 7/16; A61K 7/26
[52] U.S. Cl. ......................................... 424/49; 424/58
[58] Field of Search ..................................... 424/49–58

[56] References Cited

U.S. PATENT DOCUMENTS

| | | | |
|---|---|---|---|
| 2,184,526 | 12/1939 | Meuly | 167/94 |
| 3,666,496 | 5/1972 | Honey et al. | 99/140 R |
| 3,671,630 | 6/1972 | Carroll et al. | 424/174 |
| 3,867,557 | 2/1975 | Neely et al. | 426/175 |
| 3,928,560 | 12/1975 | Neely et al. | 424/52 |
| 3,957,964 | 5/1976 | Grimm | 424/10 |
| 4,001,438 | 1/1977 | Marmo et al. | 426/96 |
| 4,305,928 | 12/1981 | Harvey | 424/52 |

Primary Examiner—Shep K. Rose
Attorney, Agent, or Firm—Robert L. Stone; Murray M. Grill; Herbert S. Sylvester

[57] ABSTRACT

Dentifrice formulations having improved stability against discoloration upon aging comprising an unsaturated aldehyde flavoring agent selected from the group consisting of cinnamic aldehyde and citral and about 0.1–5% of a terpene or sesquiterpene color stabilizer characterized by trisubstituted double bonds and preferably selected from the group consisting of limonene and essential oils rich in limonene such as citrus oils, ocimene, caryophyllene and clove sesquiterpenes, myrcene, terpene derivatives thereof such as citronellyl acetate, and mixtures thereof, in a dental vehicle free of oxidizing agents such as peracids and salts thereof and maintained at a pH below 8.5 and preferably acid to slightly alkaline (about 5–7.5).

17 Claims, 1 Drawing Figure

FIG. 1.

STABILIZING OF CINNAMIC ALDEHYDE-CONTAINING FLAVORS WITH TERPENES AND SESQUETERPENES

BACKGROUND OF THE INVENTION

This invention relates to a color-stabilized dentifrice composition comprising a cinnamic aldehyde or citral flavorant which is subject to discoloration/yellowing upon aging, and a trisubstituted double bond-containing terpene or sesquiterpene which significantly reduces and/or prevents discoloration, and maintaining the pH of said composition below 8.5 and preferably at a neutral to acid pH. The dentifrice must be free of oxidizing agents such as hydrogen peroxide, or salts delivering hydrogen peroxide such as sodium perborate, peracids and salts of peracids.

The prior art is replete with dental formulations comprising the combination of a cinnamic aldehyde or citral flavorant and a terpene as shown in U.S. Pat. Nos. 3,867,557 and 3,928,560 wherein oral compositions containing 0.0001–20% paramethoxycinnamaldehyde flavoring agent is dissolved in 100 parts orange oil (Example VII), and 4% of the cinnamaldehyde is dissolved in 500 ml ethyl alcohol and 10 ml orange oil (Example XIII). Essential oils such as orange oil are known to contain terpenes. U.S. Pat. No. 4,001,438 also discloses flavor formulations containing citral and orange terpenes (Example B in column 10) to be used in oral compositions. However, there is no recognition in this group of patent of the discoloration or yellowing problem associated with the use of the cinnamic aldehyde flavorant. These patents relate to different aspects in dentifrice formulations. The disclosure of the combination of cinnamic aldehyde flavorant and a terpene is incidental to a general discussion of flavorants.

The prior art also recognizes the fading and/or deterioration of flavors or dyes as shown in U.S. Pat. No. 3,666,496 wherein a poly(oxyethylene)-poly(oxypropylene)copolymer is added to terpene containing flavors such as orange oil to prevent deterioration of the flavor to be used in flavored foods or beverages. U.S. Pat. No. 4,305,928 adds 0.05–5% phytic acid and/or benzoic acid as a chelator to prevent or reduce color fading of red or yellow monazo or blue triarylmethylene dye-colored visually clear dentifrice. U.S. Pat. No. 3,957,964 discloses a dentifrice containing encapsulated flavoring which provides a more stable and fresher tasting flavored dentifrice. However, there is no mention in aforesaid patents of the stabilization of the cinnamic aldehyde or citral flavor with a specific group of terpenes or sesquiterpenes characterized by a trisubstituted double bond.

U.S. Pat. No. 2,184,526 also recognizes the instability against oxidation by air of p-isopropyl-α-methylhydrocinnamic aldehyde as a perfume ingredient, wherein the aldehyde is converted into the corresponding acid, thereby destroying the aldehyde odor. The addition of alcohols of the aromatic or terpene series stabilizes the aldehyde against air oxidation, by converting the aldehyde into a hemi-acetal of said alcohol.

U.S. Pat. No. 3,671,630 discloses the use of multiple classes of terpenes as color stabilizers for aqueous halogenated phenolic germicidal compositions which discolor within a few hours of exposure to light. However, many terpenes such as limonene have been disclosed to be ineffective. The halogenated phenolic germicidal compounds cannot be equated to the cinnamic aldehyde or citral flavorants which are unsaturated aldehydes. In addition, it is noted that limonene, one of the terpenes specifically used as a color stabilizer for the flavorant, is specifically excluded as ineffective in stabilizing the germicidal composition.

None of the above cited art discloses the use of a specific group of terpenes or sesquiterpenes in a dentifrice, free of oxidizing agents and maintained at an acid or neutral pH, containing the cinnamic aldehyde or citral flavor, to reduce discoloration of said flavorant upon aging.

SUMMARY OF THE INVENTION

It has been unexpectedly found that the discoloration on aging of dentifrice products that are flavored with cinnamic aldehyde or citral can be reduced and/or prevented by the addition of a terpene or sesquiterpene characterized by trisubstituted double bonds which may be selected from the group consisting of limonene and essential oils rich in limonene, ocimene, caryophyllene and clove sesquiterpenes, myrcene, derivatives of said terpenes and mixtures thereof. It is essential that the dental vehicle be free of oxidizing agents and be maintained at an acid to neutral pH for said terpenes and sesquiterpenes to function effectively.

Accordingly, the primary object of this invention is to provide dentrifice formulations containing cinnamic aldehyde or citral flavor that does not turn yellow or discolor with age.

Another object of this invention is to provide a color stabilized dental cream or mouthwash comprising cinnamic aldehyde or citral flavor and an effective amount of a color stabilizer characterized by trisubstituted double bonds and selected from the group consisting of limonene and essential oils rich in limonene, ocimene, caryophyllene and clove sesquiterpenes, myrcene, and terpene derivatives thereof.

Still another object of this invention is to provide a color stabilized cinnamic aldehyde or citral containing dentifrice maintained at a pH below 8.5, and preferably at a neutral to acid pH.

Another object of this invention is to provide an acid or neutral color stabilized aldehyde flavorant-containing dentifrice free of oxidizing agents.

Still another object of this invention is to provide a color stabilized white dental cream or mouthrinse containing cinnamic aldehyde or citral flavorant.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the novel dentifrice of this invention, which has improved stability against discoloration upon aging, comprises an unsaturated aldehyde-containing flavorant selected from the group consisting of cinnamic aldehyde and citral which is subject to discoloration upon aging, and about 0.1–5% by weight of a terpene or sesquiterpene color stabilizer characterized by trisubstituted double bonds and preferably selected from the group consisting of limonene and essen- tial oils rich in limonene, ocimene, caryophyllene and clove sesquiterpenes, myrcene, terpene derivatives thereof, and mixtures thereof, in a dental vehicle free of oxidizing agents and maintained at a pH below 8.5, and preferably at an acid to neutral pH of about 5–7.5.

More specifically, this invention relates to a color stabilized white dental cream or mouthwash, free of oxidizing agents and having an acid to neutral pH comprising about 0.1–1% by weight of cinnamic aldehyde or citral flavorant and one or more terpenes or sesquiterpenes containing trisubstituted double bonds as the discoloration inhibitor, preferably in a 1:1 proportion.

It has been found that the cinnamic aldehyde or citral flavorant decomposed upon aging to form conjugated unsaturated aldehydes (dienals). These dienals are responsible for the yellowing or discoloration evident with cinnamic aldehyde or citral in white dental products which include liquids or creams (pastes).

Commercial dental creams utilizing low levels of cinnamic aldehyde have circumvented the discoloration problem by coloring the product, e.g. red, blue, light green, etc. However, in white dental creams, the discoloration from a low level of cinnamic aldehyde is unacceptable.

The autoxidation of cinnamic aldehyde (CA) proceeds according to the following mechanism:

The acid forms even when samples are stored in tightly capped bottles with the head space flushed with nitrogen. Cinnamaldehyde is quite sensitive to small amounts of oxygen. Since cinnamic acid is white, its formation, which occurs within a short time after exposure, is not responsible for the yellowing of cinnamaldehyde. The intensity of the yellow color increases with time of oxygen exposure, rather than with the quantity of oxygen, indicating that more complex oxidation occurs during aging. Specifically, the formation of conjugated dienals are the intensive yellow components responsible for the discoloration and yellowing of the cinnamic aldehyde.

It has now been found that discoloration from low levels of cinnamic aldehyde (a maximum of about 1% by weight) is reduced when certain terpenes or sesquiterpenes with trisubstituted double bonds are incorporated into the dentifrice composition, preferably in a 1:1 weight ratio. The terpenes include limonene (1), ocimene (2), caryophyllene (3), myrcene (4), terpene derivatives such as citronellyl acetate (5), and mixtures thereof.

Each individually at 1:1 proportions with cinnamic aldehyde significantly reduced cinnamic aldehyde discoloration on aging in a glass bottle. These compounds also reduced yellowing or aging in white dental cream, as shown in Table 1A, wherein a 40% reduction in yellowing is effected. Natural products containing these compounds can be used, such as essential oils rich in limonene, which include citrus oils such as orange, grapefruit, tangerine and mandarin oils. Clove sesquiterpenes are also effective color stabilizers.

Dental cream yellowing was measured instrumentally on the Colorgard reflectometer. Data reported on the following tables are $+\Delta b$ values (yellow scale) and represent the increase in yellow over unflavored and unaged dental cream which was taken as a zero $-b$ control. Readings taken at 3 wks, 6 and 9 wks at 120° are thought to approximate 1 yr., 2 yrs. and 3 yrs. at room temperature. It is approximated that a $\Delta b$ value of 2 to 3 is the range of marginal acceptability, as a $\Delta b$ of 2 is visually a slight off white, and a $\Delta b$ of 4 is a slight yellow-tan.

TABLE 1

| Cinnamic Aldehyde Discoloration in Dental Cream (Ex. 1) | | | |
|---|---|---|---|
| | Aging at 120° F.; $\Delta b-$ values | | |
| | 3 wks | 6 wks | 9 wks |
| A. Influence of Chemicals with Trisubstituted Double Bonds | | | |
| 1.0% Cinnamic Aldehyde (CA) | 4.5 | 7.5 | 8.0 |
| 1.0% CA + 1.0% Limonene | 2.9 | 4.9 | 5.8 |
| 1.0% CA + 1.0% Ocimene | 2.5 | 5.4 | 5.9 |
| 1.0% CA + 1.0% Caryophyllene | 3.2 | 5.3 | 6.0 |

TABLE 1-continued

| Cinnamic Aldehyde Discoloration in Dental Cream (Ex. 1) | Aging at 120° F.; Δb— values | | |
|---|---|---|---|
| | 3 wks | 6 wks | 9 wks |
| 1.0 % CA + 1.0% Citronellyl Acetate | 3.6 | 4.2 | 5.4 |
| B. Influence of pH | | | |
| 1.0% CA pH 5.0 (Citric Acid) | 4.25 | 5.5 | 5.1 |
| 1.0% CA pH 6.9 to 7.1 (Example 1) | 4.5 | 7.5 | 8.0 |
| 1.0% CA pH 8.5 (NaHCO$_3$) | 7.5 | 10.5 | 11.2 |

Figure 1:
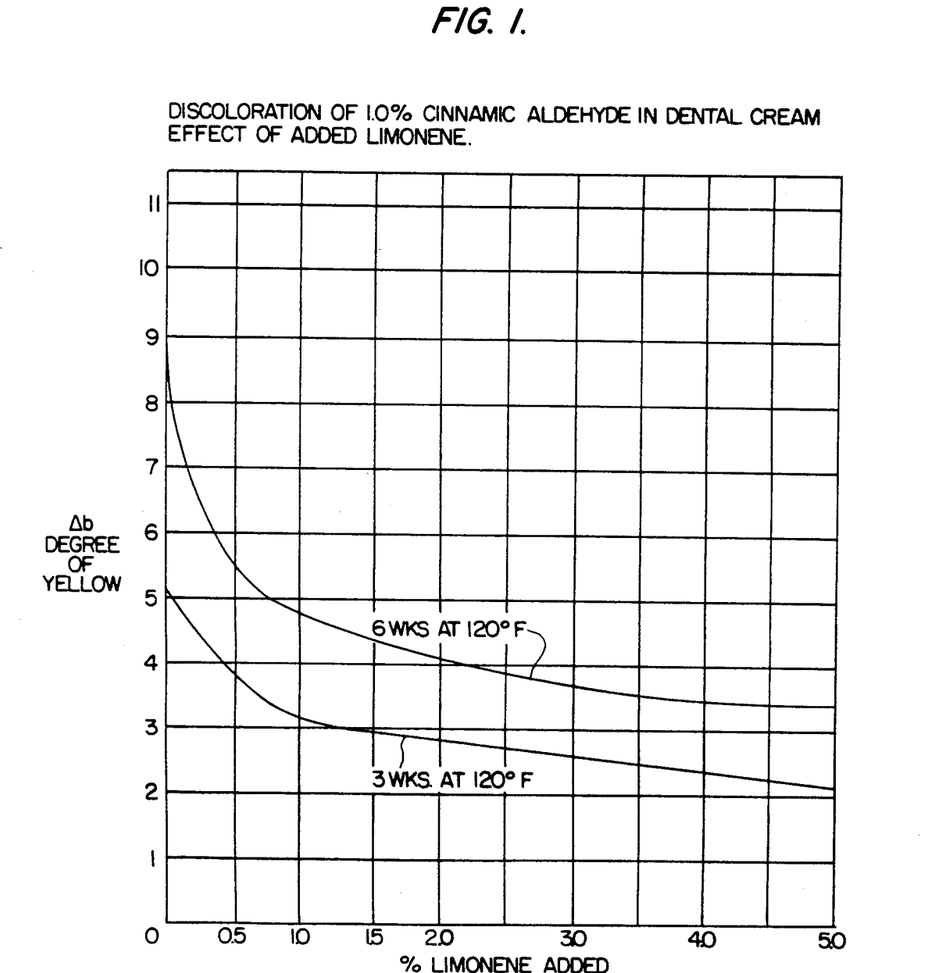

Reduction improves with increasing amount of terpene as shown with limonene in

FIG. 1, wherein is illustrated the beneficial effect of increasing amounts of limonene on the yellowing propensity of a white dental cream containing 1% cinnamic aldehyde flavorant. The vertical scale, Δb, registers the degree of yellowing from 0 (no yellowing), up to 9 (intense yellowing); and the horizontal scale defines the increasing amounts of limonene from 0 (no limonene), to 5% limonene. The lower curve represents three weeks aging at 120° F., and the upper curve represents six weeks aging at 120° F. Both curves which are parallel, indicate that the reduction of yellowing in a white dental cream increases with increasing amounts of limonene, i.e. the greater the amount of limonene, the less the degree of yellowing upon aging. Although limonene is a mild flavor (orange like) levels beyond 1% would be impractical, and may be undesirable because the orange flavor may alter the original cinnamon flavor.

The autoxidation of cinnamic aldehyde is inhibited (interrupted) by the presence of this group of terpenes and sesquiterpenes. Epoxy cinnamic aldehyde formation is prevented when limonene is added to cinnamic aldehyde. Preventing the formation of this epoxide also prevents the formation of the subsequent dienals. It was demonstrated by analytical studies that the limonene reacts preferentially over cinnamic aldehyde with the percinnamic acid to form 1,2-epoxy limonene. It is believed that the other terpenes (2, 3, 4 and 5) form similar epoxides by virtue of the trisubstituted double bond. Trisubstituted double bonds are known to have greater reactivity with peracids than mono- or disubstituted double bonds. Furthermore, cinnamic aldehyde would be expected to have less reactivity toward electrophilic attack of peracids because its double bond is substituted with an electron-withdrawing aldehyde group. Thus, by preventing the formation of the dienals, limonene significantly reduces yellowing. Other terpenes such as eugenol are ineffective in yellowing reduction.

The means for reducing discoloration of cinnamic aldehyde is also applicable to other conjugated unsaturated aldehydes such as citral, $(CH_3)_2C=CHCH_2CH_2C(CH_3)=CHCHO$. Citral is another flavor commonly used in dentifrice compositions.

Yellowing of a liquid mixture of cinnamic aldehyde or citral with a terpene additive was measured on the Gardner tintometer, both when freshly prepared and after aging for 24 hours at 90° C.±2°. Ten gram samples were prepared of mixtures of the flavorant and limonene in varying amounts, and the following readings were reported:

| | Limonene (%) | Tintometer | |
|---|---|---|---|
| | | Fresh | Aged |
| Cinnamic Aldehyde (%) | | | |
| 95 | 5 | 4¼ | 7 |
| 90 | 10 | 4¼ | 6¾ |
| 75 | 25 | 4¼ | 5 |
| 100 | 0 | (a)4½ | (a)8 |
| 50 | 50 | (a)3¾ | (a)4½ |
| Citral (%) | | | |
| 100 | 0 | (b)1½ | (b)3⅝ |
| 0 | 100 | (b)1 | — |
| 50 | 50 | (b)1 | (b)2 |

(a)Average of 2 readings
(b)Average of 3 readings

The citral alone and the 50:50 mixture of citral and limonene were additionally aged for:

| | 4 days | 6 days | 11 days |
|---|---|---|---|
| Citral alone | (b)7 | (b)7¼ | (b)9⅝ |
| 50:50 citral:limonene | (b)4 | (b)4½ | (b)5 |

The pH of the dental cream is either acid or only slightly alkaline, preferably a pH of about 5-7.5 as shown in Table 1B. The terpenes are ineffective in reducing yellowing in moderately alkaline medium. At pH 8.5 or above, the peracid anion forms and epoxidation of cinnamic aldehyde proceeds by Michael addition. This type of addition reaction cannot be intercepted by limonene.

It is also essential that the dentifrice be free of oxidizing agents such as hydrogen peroxide or salts delivering hydrogen peroxide such as sodium perborate, peracids and salts of peracids. The presence of said oxidizing agents would interfere with the preferential reaction of the terpene with the percinnamic acid in the formation of the 1,2-epoxy limonene. As discussed with reference to the necessity of maintaining an acid to neutral pH in the dental vehicle, the presence of the peracid anion proceeds to epoxidation of cinnamic aldehyde by Michael addition.

Experiments with various dental bases showed that discoloration of cinnamic aldehyde in Example 2 was approximately half that of Example 1. Also the discoloration in a bicarbonate base gave a very intense yellow. These differences were identified as being due to pH differences and also to the presence of TiO$_2$ as shown:

| | pH | TiO$_2$ |
|---|---|---|
| Example 1 | 6.9 to 7.1 | 0 |
| Example 2 | 6.15 | 0.5% |

Lowering the pH of Example 1 through the addition of either citric or phosphoric acid reduced yellowing (Table 1B). Increasing pH to 8.5 by adding NaHCO$_3$ significantly increased yellowing. It is noted that the addition of limonene had no effect on reducing the yellowing in the NaHCO$_3$ base (pH 8.5).

These observations are consistent with the autoxidation mechanism outlined. The peracid anion is formed at a pH 8.5 and epoxidation proceeds more rapidly by Michael Addition. Limonene and the other terpenes and sesquiterpenes with trisubstituted olefins are unreactive to nucleophilic addition and thus cannot scavenge the peroxide anion. Peracids are substantially weaker than the corresponding carboxylic acid. The pKa of percinnamic acid is estimated to be 7.5. In a neutral base, both free acid and anion would be present. By lowering the pH the reactions due to the anion addition would be prevented.

As noted with the Example 1 vs. Example 2 comparison, the presence of $TiO_2$ provides a reduction of yellowing both visually and instrumentally. Based on a number of comparisons with and without $TiO_2$, a $\Delta b$ reduction of 1.0 is observed with 1% $TiO_2$ and 0.5 with 0.5% $TiO_2$.

An optionally desirable additives which assists in the reduction of cinnamic aldehyde yellowing in dental formulations is titanium dioxide ($TiO_2$) in minor amounts of about 0.5-1% by weight. Table II shows the effectiveness of limonene in reducing yellowing in dental creams containing several cinnamic aldehyde containing flavors in the presence and absence of $TiO_2$.

TABLE II

| Flavor Discoloration in Dental Cream (Example 1) | | | | |
|---|---|---|---|---|
| Flavor | 1 wk | 3 wks | 6 wks | 9 wks |
| Cinnamic Aldehyde (CA) | | | | |
| 1% CA | | 4.5 | 7.5 | 8.0 |
| 1% CA + 1% Limonene + 0.5% $TiO_2$; pH 5.6 | | 2.4 | 2.9 | 4.5 |
| Spice 10 (S10)[1] | | | | |
| 1% S10 | | 3.0 | 4.2 | 4.6 |
| 1% S10 + 1% Limonene + 0.5% $TiO_2$ | | 1.9 | 2.3 | 2.6 |
| Spice 12 (12S)[2] | | | | |
| 0.8% 12S | 1 | 2.7 | 4.0 | 4.6 |
| 0.8% 12S + 0.1% Limonene | 1 | 2.1 | 3.2 | 3.9 |
| 0.8% 12S + 0.1% Limonene + 1% $TiO_2$ | — | 1.1 | 2.3 | 2.6 |
| 0.8% 12S + 0.5% Limonene + 1% $TiO_2$ | — | 0.7 | 2.0 | 2.5 |
| 0.8% 12S + 0.25% Limonene | 0.9 | 2.0 | 3.0 | 3.5 |
| 0.8% 12S + 0.5% $TiO_2$ | — | 1.5 | 2.9 | 3.1 |
| 0.8% 12S + 0.1% Limonene + 0.5% $TiO_2$ | — | 1.5 | — | 2.8 |
| 0.8% 12S + 0.1% Limonene + 0.5% $TiO_2$; pH 5.2 (citric acid) | — | 3.1 | — | 4.0 |
| 0.8% 12S + 0.25% Limonene + 0.5% $TiO_2$ | — | 1.5 | — | — |
| 0.8% 12S + 0.25% Limonene + 1% $TiO_2$ | — | 1.0 | — | — |

[1]Spice 10 Flavor contains 55% cinnamic aldehyde.
[2]Spice 12 Flavor contains 15% cinnamic aldehyde.

Other flavor compositions containing cinnamic aldehyde include:
White Spice 1—contains 30% cinnamic aldehyde.
White Spice 2—contains 25% cinnamic aldehyde.
Spice 11 Flavor—contains 55% cinnamic aldehyde.

The cinnamic aldehyde flavor compositions may be completed to 100% with flavor components such as menthol, eugenol, peppermint, spearmint, clove, anethole, methylsalicylate, vanillin and the like in various mixtures. Menthol and eugenol are not involved in the yellowing of the dental formulations.

By blending cinnamic aldehyde with limonene or other terpenes, incorporating $TiO_2$ and reducing pH, high levels of cinnamic aldehyde may be acceptable.

The flavors with cinnamic aldehyde, generally in amount of at least about 5% of the complete flavor, such as Spice 10 or Spice 12, discolor in white dental cream. If the dental cream is colored green, yellowing is not visually evident.

With Spice 10 flavor, the addition of 1% limonene and 0.5% $TiO_2$ reduced discoloration to a marginally acceptable range. This addition alters the original flavor but should be useful in achieveing similar flavors. In this case 1% $TiO_2$ and the use of caryophyllene (a spice flavor) with limonene might be preferred.

With Spice 12 flavor the amount of yellowing exceeds that expected from the 15% cinnamic aldehyde content. Interactions due to other components contribute to the discoloration. If this flavor were required for a white paste the addition of only 0.1% limonene and 1% $TiO_2$ would achieve significant color improvements and only slightly change the flavor.

The dental base utilized in present invention may be in the form of a paste, cream or liquid mouthwash, comprising known ingredients conventionally used in the dentifrice art.

Paste or cream dentifrices may be based on aqueous or substantially non-aqueous systems. The former will usually include substantial proportions of finely divided, solid polishing agent, surface active agent, gelling agent and some non-aqueous vehicle, e.g., glycerol, sorbitol, and will be opaque, whereas the latter type will often be a clear gel, containing a minor proportion of a visually clear particulate solid polishing agent, a larger proportion of non-aqueous vehicle, surface active agent and gelling agent, with a minor proportion of water often being present.

The surface active agent, or detergent, present in the dentifrice may sometimes be cationic or amphoteric but will usually be anionic or nonionic. Of these compounds, the anionics are the most preferred. The anionic detergents or surface active agents also usually serve as foaming agents. Among the useful anionic detergents may be mentioned the higher fatty acid monoglyceride monosulfates, such as the sodium salts of the monosulfated monoglycerides of hydrogenated coconut oil fatty acid; higher alkyl sulfates, such as sodium lauryl sulfate; higher alkyl aryl sulfonates, such as sodium linear dodecyl benzene sulfonate; higher olefin sulfonates, such as sodium higher olefin sulfonate in which the olefin group is 12 to 21 carbon atoms; higher alkyl potassium sulfoacetates; higher fatty acid esters of 1,2-dihydroxypropane sulfonates, magnesium salt; the substantially saturated higher aliphatic acyl amides of lower aliphatic aminocarboxylic acid alkali metal salts, such as those having 12 to 16 carbon atoms in the fatty acyl radicals, higher alkyl poly-lower alkoxy (of 10 to 100 alkoxies) sodium sulfates; higher fatty acid sodium and potassium soaps of coconut oil and tallow, and the like. As is noted, most frequently the detergents are sulfated or sulfonated compounds. Examples of useful anionic amides which may be employed are N-lauroyl sarcosine and the sodium, potassium and ethanolamine salts of N-lauroyl-, N-myristoyl- and N-palmitoyl sarcosines. In the above descriptions, "higher" refers to chain lengths of 12 to 22 carbon atoms, preferably of 12 to 18 carbon atoms and most preferably of 12 to 16 carbon atoms. Lower means 2 to 4 carbon atoms, preferably 2 to 3 carbon atoms and most preferably, two carbon atoms.

The nonionic detergents include those containing chains of lower alkylene oxide, e.g., ethylene oxide, propylene oxide, in which there are present from 10 to 100 or more moles of lower alkylene oxide. Among such materials are the block co-polymers of ethylene oxide, propylene oxide and propylene glycol, sold as Pluronics; the alkyl phenyl polyethoxy ethanols, sold as Igepals; mixed co-polymers of ethylene oxide and propylene oxide, sold as Ucons; and various other well known nonionics derived from fatty alcohols or acids and polyethylene oxide. The amphoteric or ampholytic agents include long chain (alkyl) amido-alkylene-alkalated amine derivatives, such as "Miranols," e.g. Miranol C2M; and cationic germicidal detergents, such as diisobutylphenoxyethoxyethyl dimethyl benzyl ammonium chloride; benzyl dimethyl stearyl ammonium chloride; and tertiary amines having a higher fatty alkyl group and two polyoxyethylene groups attached to the nitrogen thereof.

The detergents constitute about 0.5–5% and preferably up to 3% by weight of the dentifrice composition.

Toothpastes, dental creams and toothpowders conventionally contain substantially water insoluble polishing agents or abrasives which are compatible with the formulation, in amounts from about 20–75% by weight of the total cream or paste formulation and up to 95% in toothpowders. Suitable polishing agents include anhydrous dicalcium phosphate, dicalcium phosphate dihydrate, tricalcium phosphate, insoluble sodium metaphosphate, crystalline silica, colloidal silica, complex aluminosilicates, aluminum hydroxide (including alumina trihydrate or hydrated alumina), magnesium phosphate, magnesium carbonate, calcium carbonate, calcium pyrophosphate, bentonite, talc, calcium silicate, calcium aluminate, aluminum oxide, aluminum silicate, and silica xerogels. Most of the polishing agents mentioned are most useful in the preparation of opaque dentifrices but some of them, such as the colloidal silicas, especially the silica xerogels, and complex sodium aluminosilicates, may be utilized in the manufacture of clear dentifrices, because their indexes of refraction approximate those of the rest of the dentifrice constituents in an appropriate vehicle.

In dental cream or toothpaste dentifrice formulations, the liquids and solids should necessarily be proportioned to form a creamy mass of desired consistency which for example is extrudable from a collapsible aluminium tube. In general, the liquids in the dental cream will comprise chiefly water, glycerine, sorbitol, polyethylene glycol, or propylene glycol 400, including suitable mixtures thereof. It is advantageous usually to use a mixture of both water, and a humectant such as glycerine, or sorbitol or mixtures thereof. The total liquid content will generally be about 20–75% by weight of the formulation. It is preferred to use also a gelling agent in dental creams such as the natural and synthetic gum-like materials, e.g. Irish Moss, gum tragacanth, sodium carboxymethylcellulose, polyvinylpyrrolidone, or starch. Irish Moss and sodium carboxymethylcellulose, are compatible particularly and are preferred gelling agents. The gum content is usually in an amount up to about 10% and preferably about 0.3–5% by weight of the formulation. Fillers such as pyrogenic silica and silica aerogel may also be used, typically in amounts up to about 10% by weight to supplement the gelling agent. These colloidal silica aerogels which include Syloids 244 and 266 and Aerosil, and the pyrogenic silica sold as Cab-O-Sil may be used as gelling and thickening agents.

The liquid vehicle in the form of a mouthwash usually includes ethyl alcohol, glycerine, sorbitol, water and mixtures thereof, in an amount of about 90–98% total liquid content by weight.

Various other materials may also be incorporated into the dental vehicle. Examples thereof are fluorine-containing compounds such as stannous fluoride, potassium stannous fluoride (SnF2KP) sodium hexafluorostannate, stannous chlorofluoride, sodium fluorozirconate and sodium monofluorophosphate. These materials, which dissociate or release fluorine-containing ions in water, may be present in the dental vehicle in an effective, but nontoxic amount, usually within the range of about 0.1–5% by weight. Other additives include preservatives such as sodium benzoate, chlorophyll compounds, silicones, ammoniated materials such as urea and diammonium phosphate, antibacterial agents such as benzethonium chloride and other quaternary antibacterial compounds, sweeteners such as sodium saccharin, blue dyes, additional flavors such as peppermint or spearmint and the like. These additives may be used in amounts which do not adversely affect the properties and characteristics of the dentifrice in accordance with present invention. Each constituent may be present in minimal amounts of up to a maximum of 5% by weight and preferably up to 1% by weight of the formulation.

The dentifrice of this invention is prepared by conventional methods of making toothpaste, dental creams, mouthwashes and toothpowder. More specifically, a toothpaste may be prepared by forming a gel with carboxymethylcellulose and water, adding thereto with mixing the powdered materials and humectant, followed by the addition with mixing of polishing agent and then the surfactant and the flavor together with the terpene or sesquiterpene color stabilizer, and tubing the final mixture. The flavor composition is preferably blended with the terpene or sesquiterpene color stabilizer prior to addition to the mixture.

In the practice of this invention to promote oral hygiene, the dentifrice according to this invention is applied regularly to dental enamel by brushing the teeth for 30–90 seconds at least once daily and/or rinsing the teeth with a mouthwash once daily.

DETAILED DESCRIPTION OF THE INVENTION

The following examples are further illustrative of the nature of the present invention, but it is understood that the invention is not limited thereto. The compositions are prepared in the usual manner and all amounts and proportions referred to herein and in the appended claims are by weight unless otherwise indicated. The flavor ingredient is a cinnamic aldehyde- or citral-containing flavorant composition, to which a terpene or sesquiterpene is added as described in the experiments following the examples (Tables III through VI).

EXAMPLE 1

| Dental Cream | |
| Ingredients | % |
| --- | --- |
| Glycerine | 22.00 |
| Sodium Monofluorophosphate | 0.76 |
| Sodium Carboxymethylcellulose | 1.00 |
| Tetrasodium Pyrophosphate | 0.25 |
| Sodium Saccharin | 0.20 |
| Sodium Benzoate | 0.50 |
| Deionized Water | 24.49 |
| Dicalcium Phosphate Dihydrate | 48.76 |
| Flavor | 0.84 |
| Sodium Lauryl Sulfate | 1.20 |
| pH 6.9–7.1 | |

EXAMPLE 2

| Dental Cream | |
|---|---|
| Ingredients | % |
| Glycerine | 10.00 |
| Sodium Monofluorophosphate | 0.76 |
| Sodium Carboxymethylcellulose | 1.10 |
| Sodium Benzoate | 0.50 |
| Sodium Saccharin | 0.20 |
| Sorbitol (70% Solution) | 17.00 |
| Deionized Water | 22.19 |
| Titanium Dioxide | 0.40 |
| Insol. Sodium Metaphosphate | 39.35 |
| Hydrated Alumina | 1.00 |
| Anhy. Dicalcium Phosphate | 5.00 |
| Flavor | 1.00 |
| Sodium Lauryl Sulfate | 1.50 |

EXAMPLE 3

| Gel Dental Cream | |
|---|---|
| Ingredients | % |
| Deionized Water | 3.00 |
| Sodium Saccharin | 0.30 |
| Sodium Monofluorophosphate | 0.76 |
| Glycerine | 25.00 |
| Sodium Carboxymethylcellulose | 0.35 |
| Sodium Benzoate | 0.50 |
| Titanium Dioxide | 0.01 |
| Sorbitol (70% Solution) | 41.53 |
| Carbowax 600 (PEG 12) | 3.00 |
| Color | 0.20 |
| Sodium Alumino-silicate (silica containing combined alumina) | 18.00 |
| Colloidal Silica Aerogel | 5.50 |
| Flavor | 0.65 |
| Sodium Lauryl Sulfate | 1.20 |

EXAMPLE 4

| Toothpaste | |
|---|---|
| Ingredients | % |
| Glycerine | 25.00 |
| Sodium Carboxymethylcellulose | 1.40 |
| Sodium Benzoate | 0.50 |
| Sodium Saccharin | 0.20 |
| Sodium Monofluorophosphate | 0.76 |
| Deionized Water | 35.44 |
| Titanium Dioxide | 0.40 |
| Aluminum oxide | 10.00 |
| Silica | 24.00 |
| Flavor | 1.10 |
| Sodium Lauryl Sulfate | 1.20 |
| pH 6.2 ± 0.5 | |

EXAMPLE 5

Example 4 is repeated except that the sodium lauryl sulfate is increased to 1.5% and the water content adjusted accordingly.

EXAMPLE 6

| Mouthwash | |
|---|---|
| Ingredients | % |
| Ethyl Alcohol | 15-30 |
| Glycerine | 10-15 |
| Polysorbate 80[1] | 2-3 |
| Poloxamer 338[2] | 0-0.5 |
| Benzethonium Chloride | 0-0.075 |
| Flavor Composition | 0.1-0.5 |
| Deionized Water | Balance |

[1] A mixture of oleate esters of sorbitol and sorbital anhydrides, consisting of the monoester condensed with approximately 20 moles of ethylene oxide.
[2] The polyoxyethylene polyoxypropylene block polymer that conforms to the formula:

wherein x and z = 128, and y = 54.

Flavor levels in mouthwash are generally less than in a dental cream.

EXAMPLE 7

| Dental Powder | |
|---|---|
| Ingredients | % |
| Magnesium Silicate | 7.00 |
| Sodium Saccharin | 0.15 |
| Flavor | 2.50 |
| Dicalcium Phosphate-Anhy. | 88.35 |
| Sodium Lauryl Sulfate | 2.00 |

Flavor levels in dental powders are generally greater than in dental creams.

The following tables represent discoloration results upon aging at 120° F. of the dental cream of Example 1 unless otherwise specified, both unflavored and containing cinnamic aldehyde (CA) flavorant per se and with specific terpenes or sesquiterpenes containing a trisubstituted double bond to prevent or reduce the discoloration caused by the cinnamic aldehyde ingredient.

The b values in the tables represent the dental cream yellowing measured on the Colorgard reflectometer and the Δb value represents the increase in yellowing from the unaged and unflavored sample which is the zero b control.

TABLE III

Dental Cream Discoloration Studies
120° F. Aging in Dental Cream of Example 1

| | Control | | 3 wks | | 4 wks | | 5 wks | | 6 wks | | 7 wks | | 9 wks | |
|---|---|---|---|---|---|---|---|---|---|---|---|---|---|---|
| | b | Δb | b | Δb | b | Δb | b | Δb | b | Δb | b | Δb | b | Δb |
| Experiment I | | | | | | | | | | | | | | |
| 0.5% CA | | | | | | | 5.2 | +2.5 | 5.7 | +3.9 | | | 6.6 | +4.8 |
| | | | | | | | 5.5 | +2.8 | | | | | 6.6 | +4.8 |
| 0.5% CA + 0.5% Limonene | | | | | | | 5.2 | +2.5 | 6.0 | +4.2 | | | 6.7 | +4.9 |
| | | | | | | | 5.6 | +2.9 | | | | | 6.9 | +5.1 |
| Unflavored | 2.7 | | | | | | 2.9 | +0.2 | 2.7 | +0.9 | | | 2.9 | +1.1 |
| Experiment II | | | | | | | | | | | | | | |
| 0.5% CA | 1.9 | +0.2 | | | 4.6 | +2.6 | 4.9 | +3.1 | | | 5.7 | +3.8 | 6.4 | +4.5 |
| 0.5% CA + 0.5% | | | | | 6.2 | +4.2 | 7.6 | +5.8 | | | 7.7 | +5.8 | 9.5 | +7.6 |

TABLE III-continued

Dental Cream Discoloration Studies
120° F. Aging in Dental Cream of Example 1

| | Control | | 3 wks | | 4 wks | | 5 wks | | 6 wks | | 7 wks | | 9 wks | |
|---|---|---|---|---|---|---|---|---|---|---|---|---|---|---|
| | b | Δb | b | Δb | b | Δb | b | Δb | b | Δb | b | Δb | b | Δb |
| Eugenol | | | | | | | | | | | | | | |
| 0.5% CA in Ex. 2 | | | | | 3.3 | +1 | 3.7 | +1.9 | | | separation | | separation | |
| 0.5% CA +0.5% Eugenol in Ex. 2 | | | | | 3.8 | +1.9 | 4.3 | +2.5 | | | 4.8 | +2.9 | 5.6 | +3.7 |
| Unflavored Ex. 2 | 2.0 | 1.8 | | | | | | | | | | | | |
| | 1.9 | 1.9 | | | | | | | | | | | | |
| Experiment III | | | | | | | | | | | | | | |
| 1% CA | | | 6.6 | +3.9 | 7.6 | +5.4 | | | | | 9.3 | +7.1 | 10.5 | +9 |
| | | | | | | | | | | | | | 9.9 | +8.4 |
| 1% CA + 1% Limonene | | | 4.9 | +2.2 | 5.4 | +3.2 | | | | | 6.5 | +4.4 | 7.5 | +6 |
| | | | | | | | | | | | | | 6.9 | +5.4 |
| 1% CA + 2% Limonene | | | 4.5 | +1.8 | 4.8 | +2.6 | | | | | 5.7 | +3.6 | 6.2 | +4.7 |
| | | | | | | | | | | | | | 5.8 | +4.3 |
| Unflavored | 2.7 | 0 | | | | | | | | | | | | |
| Experiment IV | | | | | | | | | | | | | | |
| 1% CA | | | 5.7 | +3.6 | | | | | | | 9.2 | +7.3 | 9.9 | +8.1 |
| 1% CA + 1% Ocimene | | | 4.6 | +2.5 | | | | | | | 7.3 | +5.4 | 7.7 | +5.9 |
| 1% CA + 2% Ocimene | | | 5.1 | +3 | | | | | | | 7 | +5.1 | 7.7 | +5.9 |
| 2% Ocimene | | | 3 | +0.9 | | | | | | | 3.8 | +1.9 | 3.9 | +2.1 |
| Unflavored | 2.1 | | 2.1 | | | | | | | | 2.1 | +0.2 | 2 | +0.2 |

TABLE IV

120° F. Aging in Dental Cream of Example 1

| | Control | | 2 wks | | 3 wks | | 4 wks | | 6 wks | | 9 wks | |
|---|---|---|---|---|---|---|---|---|---|---|---|---|
| | b | Δb | b | Δb | b | Δb | b | Δb | b | Δb | b | Δb |
| Experiment V | | | | | | | | | | | | |
| 1% CA | | | | | 6.7 | +4.8 | | | 8.4 | +6.5 | 9.6 | +7.9 |
| | | | | | | | | | | | 10.2 | +8.5 |
| 1% Eugenol | | | | | 4.1 | +2.2 | | | 4.5 | +2.6 | 4.3 | +2.6 |
| 1% CA + 1% Eugenol | | | | | 8.1 | +6.2 | | | 9.9 | +8 | 10.7 | +9 |
| 0.5% CA + 0.5% Eugenol | | | | | 5.9 | +4 | | | 8.1 | +6.2 | 8.9 | +7.2 |
| 0.9% CA + 0.1% Eugenol | | | | | 5 | +3.1 | | | 6.6 | +4.7 | 7.2 | +5.5 |
| 1% Spice 10 | | | | | 4.8 | +2.9 | | | 6.3 | +4.4 | 6.7 | +5 |
| | | | | | | | | | | | 6.4 | +4.7 |
| 10% White Spice #1 | | | | | 3.8 | +1.9 | | | 4.6 | +2.7 | 5.0 | +3.3 |
| | | | | | | | | | | | 5.1 | +3.4 |
| Unflavored | 1.9 | | | | | | | | | | | |
| Experiment VI | | | | | | | | | | | | |
| 1% White Spice #2 | | | 3.3 | +1.2 | 3.5 | +1.7 | | | 4.6 | +2.9 | 5.1 | +3.2 |
| | | | | | | | | | 4 | +2.3 | | |
| Unflavored | 2.1 | | 2.1 | 0 | | | | | 2.2 | +0.5 | 2 | +0.1 |
| Experiment VII | | | | | | | | | | | | |
| 0.5% CA + 0.5% Eugenol | | | 5.9 | +4 | | | | | 7.2 | +5.3 | 7.8 | +6 |
| | | | | | | | | | 6.9 | +5.0 | 7.8 | +6 |
| 0.5% CA + 0.5% Eugenol + 1% Limonene | | | 4.7 | +2.8 | | | | | 6 | +4.1 | 7 | +5.2 |
| | | | | | | | | | 6 | +4.1 | 7.5 | +5.7 |
| Unflavored | 1.9 | | | | | | | | | | | |
| Experiment VIII | | | | | | | | | | | | |
| 1% White Spice #1 | | | | | | | 4.1 | +1.9 | 4.8 | +3.0 | 5.1 | +3.5 |
| 1% Spice 10 | | | | | | | 5.6 | +3.4 | 5.8 | +4.2 | 5.8 | +3.8 |
| | | | | | | | | | 5.6 | +4.0 | 6 | +4.4 |
| 1% Spice 10 + 1% Limonene | | | | | | | 4.9 | +2.7 | 4.8 | +3.2 | 5 | +3 |
| | | | | | | | | | 5.2 | +3.6 | 5.4 | +3.8 |
| 1% Spice 11 + 1% Limonene | | | | | | | 4.8 | +2.6 | 5.1 | +3.5 | 5.3 | +3.7 |
| | | | | | | | | | 5.4 | +3.8 | | |
| 1% Limonene | | | | | | | 2.4 | +0.2 | 2.3 | +0.5 | 1.9 | +0.3 |

TABLE V

120° F. Aging in Dental Cream of Example 1

| | Control | | 1 wk | | 2 wks | | 3 wks | | 6 wks | | 9 wks | |
|---|---|---|---|---|---|---|---|---|---|---|---|---|
| | b | Δb | b | Δb | b | Δb | b | Δb | b | Δb | b | Δb |
| Experiment IX | | | | | | | | | | | | |
| 1% CA | | | 4.5 | +2.5 | | | 7.2 | +5.1 | 10.5 | +8.9 | 11.1 | +9.2 |
| 1% CA + 0.25% Limonene | | | | | | | 6.1 | +4 | 7.7 | +6.1 | 8.5 | +6.6 |
| 1% CA + 0.5% Limonene | | | | | | | 5.9 | +3.8 | 6.9 | +5.3 | 8.3 | +6.4 |
| 1% CA + 0.75% Limonene | | | | | | | 5.4 | +3.3 | 6.9 | +5.3 | 7.8 | +5.9 |
| 1% CA + 1% Limonene | | | | | | | 5.3 | +3.2 | 6.5 | +4.9 | 7.9 | +6 |
| 1% CA + 1.5% Limonene | | | | | | | 5.0 | +2.9 | 6.6 | +5.0 | 6.7 | +4.8 |
| 1% CA + 3% Limonene | | | | | | | 4.8 | +2.7 | 5.3 | +3.7 | 6.2 | +4.3 |
| 1% CA + 5% Limonene | | | | | | | 4.2 | +2.1 | 5.0 | +3.4 | 5.7 | +3.8 |

TABLE V-continued

| | 120° F. Aging in Dental Cream of Example 1 | | | | | | | | | | | |
|---|---|---|---|---|---|---|---|---|---|---|---|---|
| | Control | | 1 wk | | 2 wks | | 3 wks | | 6 wks | | 9 wks | |
| | b | Δb | b | Δb | b | Δb | b | Δb | b | Δb | b | Δb |
| Unflavored | 2.1 | | | | | | | | | | | |
| 1% CA + 1% Caryophyllene | | | 3.3 | +1.3 | | | 5.3 | +3.2 | 6.9 | +5.3 | 7.9 | +6 |
| Experiment X | | | | | | | | | | | | |
| Example 4 | 1.5 | | | | 1.8 | +0.3 | 1.8 | | 2.1 | +0.4 | 2.1 | +0.2 |
| Example 4 | | | | | | | 1.8 | −0.2 | 1.6 | | 1.8 | −0.1 |
| Example 1 | 2.3 | | | | 2.6 | +0.3 | | | 2.7 | +1 | 3.0 | +1.1 |
| Example 1 | | | | | | | 2.5 | +0.5 | 2.3 | +0.7 | 2.3 | +0.4 |
| Example 2 Unflavored | 1.6 | −0.3 | | | | | 1.7 | −0.3 | | | 1.5 | −0.4 |
| Example 1 Unflavored | 1.9 | | | | | | 2.1 | +0.1 | | | 1.9 | |
| Example 5 Unflavored | 1.5 | −0.4 | | | | | 1.9 | −0.1 | | | 1.8 | −0.1 |
| Experiment XI | | | | | | | | | | | | |
| 1% White Spice 11 + 1% | | | 2.9 | +1.2 | | | 4.6 | +2.9 | 5.3 | +3.7 | 5.5 | +3.6 |
| Limonene in Example 5 | 1.9 | | 2.9 | +1.2 | | | 4.5 | +2.8 | 5.2 | +3.6 | 5.4 | +3.5 |
| 0.5% CA | 2.3 | +0.1 | 3.1 | +1.4 | | | 4.5 | +2.9 | 6.1 | +4.5 | 6.0 | +4.1 |

TABLE VI

| | 120° F. Aging in Dental Cream of Example 1 | | | | | | | | | | | |
|---|---|---|---|---|---|---|---|---|---|---|---|---|
| | Control | | 1 wk | | 3 wks | | 5 wks | | 6 wks | | 9 wks | |
| | b | Δb | b | Δb | b | Δb | b | Δb | b | Δb | b | Δb |
| Experiment XII | | | | | | | | | | | | |
| 1% CA in Ex. 1 pH 4.9 | | | 3.1 | +1.3 | 6.3 | +4.5 | | | 7.4 | +5.5 | 7.2 | +4.8 |
| 1% CA in Ex. 1 pH 6.9 | | | 4 | +2.2 | 7 | +5.2 | | | 8.9 | +7 | 8.3 | +5.9 |
| Ex. 1 Unflavored pH 4.9 | | | 1.6 | | 1.8 | | | | 1.9 | | 2.4 | |
| Ex. 1 Unflavored pH 6.9 | | | 1.8 | | | | | | 1.9 | | 2.2 | |
| Ex. 2 Unflavored | 1.6 | | | | | | | | | | | |
| Experiment XIII | | | | | | | | | | | | |
| 0.8% Spice 12 + 0.5% TiO₂ + 0.1% Limonene | | | | | 2.9 | +1.1 | 3.6 | +1.9 | | | 4.9 | +2.8 |
| Above at pH 5.2 (Citric Acid) | | | | | 4.9 | +3.1 | 5.3 | +3.6 | | | 6.1 | +4.0 |
| Above at pH 5.1 (H₃PO₄) | | | | | 4.7 | +2.9 | 5 | +3.3 | | | | |
| Above at pH 6.2 (H₃PO₄) | | | | | 4.4 | +2.6 | 4.9 | +3.2 | | | | |
| Above at pH 5.8 (Citric) | | | | | 4.7 | +2.9 | 5.2 | +3.5 | | | 5.7 | +3.6 |
| 1% Spice 10 + 0.5% TiO₂ + 1% Limonene | | | 2.7 | +0.9 | 3.8 | +2.1 | 4.2 | +2.5 | | | 4.7 | +2.6 |
| | | | | | 3.6 | +2.0 | | | | | | |
| Above at pH 5.2 (Citric Acid) | | | 2.6 | +0.8 | 3.5 | +1.9 | 3.8 | +2.1 | | | 4.6 | +2.5 |
| Above at pH 5.1 (H₃PO₄) | | | 2.8 | +1.0 | 3.7 | +2 | 4.3 | +2.6 | | | 5.6 | +2.5 |
| | | | | | 3.2 | +1.6 | | | | | | |
| Above at pH 5.8 (Citric) | | | 2.8 | +1 | 3.7 | +2.1 | 4.1 | +2.4 | | | 5.3 | +3.2 |
| Above at pH 6.2 (H₃PO₄) | | | 2.8 | +1 | 3.8 | +2.2 | 4.1 | +2.4 | | | 4.6 | +2.5 |
| Experiment XIV | | | | | | | | | | | | |
| 1% CA in Ex. 2 | | | | | 5.2 | +3.5 | | | 6.9 | +4.7 | 7.1 | +5.3 |
| 1% CA + 1% Limonene in Ex. 2 | | | | | 4.2 | +2.5 | | | 5.2 | +3.0 | 5.8 | +4.0 |
| Duplicate Sample | | | | | 4.4 | +2.7 | | | 5.2 | +3.0 | 5.8 | +4.0 |
| 1% Citral | | | | | 4.9 | +3.2 | | | 5.4 | +3.2 | 6.2 | +4.4 |
| 1% Citral + 1% Limonene | | | | | 3.7 | +2.0 | | | 4.3 | +2.1 | 4.8 | +3.0 |
| 1% CA + 0.5% TiO₂ pH 5.6 | | | | | 5.2 | +3.5 | | | 6.9 | +4.7 | 6.7 | +4.9 |
| 1% CA + 1% Limonene +0.5% TiO₂ pH 5.6 | | | | | 4.1 | +2.4 | | | 5.1 | +2.9 | 6.1 | +4.5 |
| 08.% Spice 12 + 0.5% TiO₂ pH 5.6 | | | | | 4.3 | +2.7 | | | 5.2 | +3.0 | 5.7 | +3.9 |
| 0.8% Spice 12 + 0.1% Limonene + 0.5% TiO₂ pH 5.6 | | | | | 4.2 | +2.6 | | | 5.3 | +3.1 | 5.9 | +4.1 |

Tables III to VI inclusive disclose formulations containing a variety of flavorants containing cinnamic aldehyde and citral which yellow upon aging, and the reduction of said yellowing by the addition of limonene or other terpenes and sesquiterpenes characterized by trisubstituted double bonds. The adjustment of the pH to about 6 and the addition of TiO₂ further reduce the yellowing of these flavor-containing formulations.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A white dentifrice formulation having improved stability against yellowing discoloration upon aging, comprising about 0.1–1% by weight of an unsaturated aldehyde-containing flavorant selected from the group consisting of cinnamic aldehyde and citral, which is subject to discoloration with aging, and about 0.1–5% by weight of at least one terpene or sesquiterpene containing trisubstituted double bonds effective to impart color stability against aging, in a dental vehicle free of oxidizing agents and having a slightly acid to alkaline pH below 8.5.

2. The dentifrice, according to claim 1, wherein the discoloration inhibitor is selected from the group consisting of limonene, ocimene, caryophyllene and cloves sesquiterpenes, myrcene, terpene derivatives thereof, and mixtures thereof.

3. The dentifrice according to claim 2 wherein the amount of said aldehyde flavorant to terpene is in a 1:1 weight ratio.

4. The dentifrice according to claim 2, wherein the dentifrice is a dental vehicle having a pH of about 5 to 7.5.

5. The dentifrice according to claim 4, wherein the dentifrice is a white color stabilized dental cream containing about 20-75% by weight of a water-insoluble polishing agent.

6. The dentifrice according to claim 5, which additionally contains about 0.5-1% by weight of titanium dioxide.

7. The dentifrice according to claim 4, wherein the dentifrice is a white color stabilized mouthwash, containing a liquid content of about 90-98% by weight.

8. The dental cream according to claim 5 containing 1% cinnamic aldehyde flavor and 1% limonene color stabilizer.

9. The dental cream according to claim 5 containing 1% cinnamic aldehyde flavor and 1% ocimene color stabilizer.

10. The dental cream according to claim 5 containing 1% cinnamic aldehyde flavor and 1% caryophyllene color stabilizer.

11. The dental cream according to claim 5, containing 1% cinnamic aldehyde flavor and 1% citronellyl acetate color stabilizer.

12. The dental cream according to claim 5 containing 1% citral flavor and 1% limonene color stabilizer.

13. The dental cream according to claim 6 containing 1% cinnamic aldehyde flavor and 1% limonene color stabilizer.

14. The mouthwash according to claim 7 containing 0.1-0.5% by weight of a flavor composition containing cinnamic aldehyde or citral.

15. A dental cream according to claim 6 containing 0.1-1% by weight of a flavor composition containing cinnamic aldehyde or citral.

16. A dentifrice according to claim 1 containing about 0.05-5% surfactant.

17. The dental cream according to claim 5, containing a liquid content of about 20-75% by weight of the composition.

* * * * *